US011918791B2

United States Patent
McLusky et al.

(10) Patent No.: US 11,918,791 B2
(45) Date of Patent: Mar. 5, 2024

(54) GRIP ACCESSORY FOR A MANUAL INJECTION DEVICE

(71) Applicant: Janssen Pharmaceuticals, Inc., Titusville, NJ (US)

(72) Inventors: James McLusky, Edinburgh (GB); Nick Foley, Edinburgh (GB); Jimmy Mower, Edinburgh (GB); Ian Scrimgeour, Dunbar (GB); Michael Cannamela, Atlantic Highlands, NJ (US); Peter Krulevitch, Pleasanton, CA (US); Kui Liu, Redwood City, CA (US)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 133 days.

(21) Appl. No.: 16/617,119

(22) PCT Filed: May 29, 2018

(86) PCT No.: PCT/US2018/034849
§ 371 (c)(1),
(2) Date: Nov. 26, 2019

(87) PCT Pub. No.: WO2018/222574
PCT Pub. Date: Dec. 6, 2018

(65) Prior Publication Data
US 2021/0290855 A1    Sep. 23, 2021

(30) Foreign Application Priority Data
May 30, 2017  (GB) ..................... 1708593

(51) Int. Cl.
*A61M 5/315*   (2006.01)
*A61M 5/31*    (2006.01)
*A61M 5/32*    (2006.01)

(52) U.S. Cl.
CPC ...... *A61M 5/31566* (2013.01); *A61M 5/3137* (2013.01); *A61M 5/326* (2013.01);
(Continued)

(58) Field of Classification Search
CPC ........ A61M 2005/3139; A61M 5/3137; A61M 5/326; A61M 5/31566; A61M 2005/3264; A61M 2005/3267
See application file for complete search history.

(56) References Cited

U.S. PATENT DOCUMENTS

| 5,163,918 A | 11/1992 | Righi et al. |
| 5,215,533 A * | 6/1993 | Robb ...................... A61M 5/50 604/110 |

(Continued)

FOREIGN PATENT DOCUMENTS

| EM | 004024677-0002 | 5/2017 |
| EM | 004024677-0003 | 5/2017 |

(Continued)

OTHER PUBLICATIONS

U.S. Appl. No. 29/676,220, Janssen Pharmaceuticals, Inc.
(Continued)

*Primary Examiner* — Jason E Flick
*Assistant Examiner* — Justin L Zamory
(74) *Attorney, Agent, or Firm* — Craig M. Brown

(57) ABSTRACT

A grip accessory for a manual injection device comprises a housing having a generally hollow body for supporting a manual injection device therein. The housing comprises a distal portion comprising a first opening into which a manual injection device can be inserted, a proximal portion comprising a second opening through which a needle of the manual injection device is extendable, the proximal portion comprising a skin contacting surface at a proximal end of the device. An intermediate portion extends between the proxi-
(Continued)

mal and distal portions and guide means is provided on an interior surface of the distal portion for guiding a plunger rod of an injection device during delivery of an injection.

19 Claims, 7 Drawing Sheets

(52) U.S. Cl.
CPC .............. *A61M 2005/3139* (2013.01); *A61M 2005/3267* (2013.01)

(56) References Cited

U.S. PATENT DOCUMENTS

| | | | |
|---|---|---|---|
| 6,159,184 A | 12/2000 | Perez et al. | |
| 6,171,283 B1 | 1/2001 | Perez et al. | |
| D446,578 S | 8/2001 | Janse | |
| 6,344,032 B1 | 2/2002 | Perez et al. | |
| 6,623,459 B1 | 9/2003 | Doyle | |
| 7,041,085 B2 | 5/2006 | Perez et al. | |
| 7,824,379 B2 | 11/2010 | Doyle | |
| D634,424 S | 3/2011 | Morejon | |
| D673,677 S | 1/2013 | Noda | |
| D702,835 S | 4/2014 | Vinchon | |
| D720,070 S | 12/2014 | Khalaj | |
| 8,974,424 B2 | 3/2015 | Soma | |
| D770,612 S | 11/2016 | Green | |
| D784,524 S | 4/2017 | Corbin | |
| D784,526 S | 4/2017 | Grunhut | |
| D784,527 S | 4/2017 | Llewellyn-Hyde | |
| D816,834 S | 5/2018 | Knight | |
| D816,835 S | 5/2018 | Knight | |
| D818,575 S | 5/2018 | Corbin | |
| D819,805 S | 6/2018 | Knight | |
| D830,540 S | 10/2018 | Rolfs | |
| 10,272,202 B2 | 4/2019 | Brereton et al. | |
| D872,259 S | 1/2020 | Guo | |
| D888,941 S | 6/2020 | Scrimgeour et al. | |
| D902,391 S | 11/2020 | Scrimgeour et al. | |
| D902,392 S | 11/2020 | Scrimgeour et al. | |
| D903,108 S | 11/2020 | Scrimgeour et al. | |
| 2002/0161337 A1 | 10/2002 | Shaw et al. | |
| 2003/0093032 A1 | 5/2003 | Py et al. | |
| 2003/0144631 A1 | 7/2003 | Doyle et al. | |
| 2003/0144632 A1 | 7/2003 | Hommann | |
| 2005/0033242 A1 | 2/2005 | Perez et al. | |
| 2005/0054987 A1 | 3/2005 | Perez et al. | |
| 2006/0036216 A1 | 2/2006 | Rimlinger et al. | |
| 2006/0089594 A1 | 4/2006 | Landau | |
| 2006/0106342 A1 | 5/2006 | Cox | |
| 2007/0047200 A1 | 3/2007 | Huang | |
| 2007/0073224 A1 | 3/2007 | Dries | |
| 2007/0239117 A1 | 10/2007 | Chelak | |
| 2008/0208140 A1* | 8/2008 | Barrelle | A61M 5/326 604/198 |
| 2008/0269692 A1* | 10/2008 | James | A61M 5/3243 604/198 |
| 2008/0300549 A1 | 12/2008 | Verespej et al. | |
| 2009/0043262 A1 | 2/2009 | Snow | |
| 2011/0092915 A1 | 4/2011 | Olson et al. | |
| 2012/0232491 A1 | 9/2012 | Jennings | |
| 2013/0116624 A1 | 5/2013 | Plunnecke | |
| 2013/0184655 A1 | 7/2013 | Lanzi et al. | |
| 2013/0197446 A1 | 8/2013 | Gustafsson | |
| 2013/0289524 A1 | 10/2013 | Crawford | |
| 2014/0039406 A1* | 2/2014 | Verespej | A61M 5/28 604/194 |
| 2014/0039407 A1 | 2/2014 | Schoonmaker | |
| 2014/0296782 A1 | 10/2014 | Ulrich et al. | |
| 2014/0343505 A1 | 11/2014 | Henley et al. | |
| 2015/0174340 A1 | 6/2015 | Torris et al. | |
| 2016/0325047 A1 | 11/2016 | Vedrine | |
| 2017/0014574 A1 | 1/2017 | Ogawa | |
| 2017/0157332 A1 | 6/2017 | Nguyen | |
| 2017/0157334 A1 | 6/2017 | Nguyen | |
| 2017/0173270 A1* | 6/2017 | Nakamura | A61M 5/3257 |
| 2019/0111218 A1 | 4/2019 | Beyers et al. | |

FOREIGN PATENT DOCUMENTS

| | | |
|---|---|---|
| EM | 004024677-0004 | 5/2017 |
| EP | 2623145 | 8/2013 |
| EP | 2588167 | 2/2018 |
| EP | 2588167 B1 | 2/2018 |
| FR | 3025433 | 3/2016 |
| GB | 2308302 | 11/1997 |
| JP | D1341211 | 9/2008 |
| JP | D1341392 | 9/2008 |
| JP | D1354787 | 2/2009 |
| JP | 2015/62563 | 4/2015 |
| JP | D1557827 | 8/2016 |
| JP | D1558612 | 8/2016 |
| JP | 2016-526996 | 9/2016 |
| JP | D1564673 | 11/2016 |
| JP | D1565060 | 11/2016 |
| JP | 2016-540584 | 12/2016 |
| JP | D1571037 | 2/2017 |
| JP | D1571038 | 2/2017 |
| JP | D1571040 | 2/2017 |
| JP | 2021-1520901 | 8/2021 |
| KR | 300876368 | 10/2016 |
| KR | 300891458 | 1/2017 |
| RU | 2620353 | 5/2017 |
| WO | WO 1995/007722 | 3/1995 |
| WO | 1999017823 A1 | 4/1999 |
| WO | WO 2001/085239 | 11/2001 |
| WO | WO 2001/085239 A2 | 11/2001 |
| WO | WO 2004/069302 | 8/2004 |
| WO | WO 2007/047200 | 4/2007 |
| WO | WO 2008/016381 | 2/2008 |
| WO | WO 2010/104779 | 9/2010 |
| WO | WO 2015/0007857 | 1/2015 |
| WO | WO 2015/044561 | 4/2015 |
| WO | WO 2015/091850 | 6/2015 |
| WO | WO 2015/122884 | 8/2015 |
| WO | WO 2017/089266 | 6/2017 |
| WO | WO 2018/075335 | 4/2018 |
| WO | WO 2018/075335 A1 | 4/2018 |
| WO | WO 2018/222574 | 12/2018 |
| WO | WO 2018/222575 | 12/2018 |
| WO | WO 2019/0197381 | 10/2019 |
| WO | WO 2019/231432 | 12/2019 |

OTHER PUBLICATIONS

U.S. Appl. No. 29/627,912, Janssen Pharmaceuticals, Inc.
International Search Report dated Sep. 3, 2018; International Application No. PCT/US2018/034850.
International Search Report dated Aug. 30, 2018; International Application No. PCT/US2018/034849.
International Search Report dated Aug. 21, 2018; International Application No. PCT/US2018/034852.
International Trademark No. 1143335-S, Safety Syringes, Inc., Feb. 17, 2012.
D. Prajapati, 2015, "BD Ultrasafe Hi Res", https://www.youtube.com/watch?v=VxL1VFYAbhl.

* cited by examiner

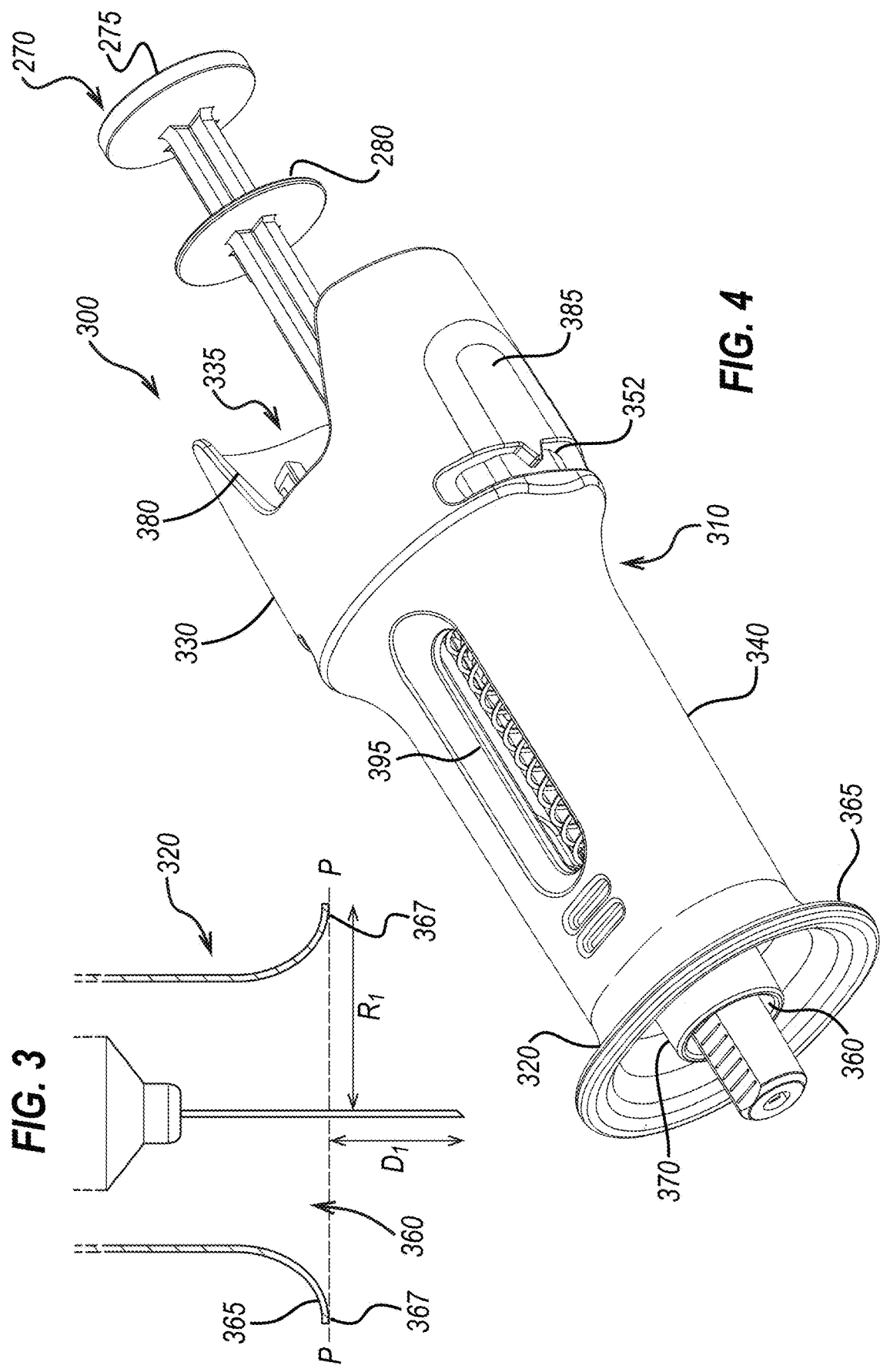

GRIP ACCESSORY FOR A MANUAL INJECTION DEVICE

CROSS REFERENCE TO RELATED APPLICATIONS

This application is the national stage of PCT Application No. PCT/US2018/034849, filed May 29, 2018, which claims priority from GB Application No. 1708593.7 filed May 30, 2017, the entire disclosures of which are hereby incorporated by reference in their entirety.

FIELD OF THE INVENTION

The present invention is related to accessories for manual injection devices, specifically a grip accessory for use with a manual injection device.

BACKGROUND OF THE INVENTION

Needle safety devices are commonly used in combination with syringes when performing injections, in order to reduce the risk of accidental needle sticks which can result in transmission of blood borne pathogens. In particular these needle safety devices are often required to protect Health Care Providers such as nurses who frequently use syringes to administer injections to patients. These needle safety devices typically can be categorized as one of two types: (1) passive devices that automatically cover the needle after the injection, without requiring additional steps from the user in order to activate the device, and (2) devices that require an additional step by the user in order to activate the needle safety feature. Passive needle safety devices generally are considered to be superior in their ability to protect the user from accidental needle sticks, because, for various reasons, users may fail to take the additional actions required to activate non-passive devices. Health authorities and health care systems often require the use of needle safety devices in settings where Health Care Providers (HCPs) perform injections. Furthermore, needle safety devices are desirable for self- and caregiver-administered injections to mitigate the risk for injury, infection, and the spread of blood borne pathogens to patients, family members, caregivers and anyone who might come in contact with the injection devices in the process of performing the injection and disposing of used syringes.

A commonly used example of needle safety devices is the UltraSafe family of devices, manufactured by Becton Dickinson. The UltraSafe consists of two plastic components and a spring that are assembled to the syringe, along with a custom plunger rod. Upon completion of the injection, the plunger rod engages latches on the UltraSafe housing components, activating the device and causing the spring to extend one of the housing components over the needle and lock into place. An example of an UltraSafe device is shown in FIGS. 1A and 1B. FIG. 1A shows the device in a ready state, before an injection takes place. FIG. 1B shown the device in a safe, used state, after an injection has been completed.

FIG. 2 shows the typical instructions for using the UltraSafe device. As can be seen in FIG. 2, the steps for using UltraSafe are essentially the same as for performing an injection with a bare syringe. Pinching the skin and injecting at a 45 degree angle (shown in step (A) of FIG. 2) are essential to limit the depth of injection and ensure that the injection is given subcutaneously and not into the muscle (too deep) or intradermally (into the skin). Injecting too shallow or too deep can impact the pharmacokinetics (PK) and pharmacodynamics (PD) for drugs that are intended for subcutaneous injection.

As shown in FIG. 2, the steps for proper use of a syringe to achieve a subcutaneous injection are actually fairly complex, and variation from user to user can result in differences in the depth of injection, which can impact the efficacy of the drug. HCPs such as nurses are quite familiar and practiced with the procedure for performing injections with syringes. However, technique does vary from nurse to nurse, which can impact PK and PD. Moreover, the injection technique requires the use of two hands, one to pinch and one to inject, making it difficult for nurses to perform the injection on difficult patients such as pediatrics who may move during the injection. Furthermore, even though the nurse is comfortable using a syringe, patients are often scared of the syringe and needle, and the injection often results in an unpleasant patient experience.

Syringes are especially difficult for patients and caregivers to use, not only because of the complexity of the use steps (as described above), but also because syringes with exposed needles tend to cause anxiety for the patient.

Thus, there is a need to develop a needle safety device that is inexpensive, simple and easy to use, can be operated with one hand, results in consistent needle insertion depth, and reduces injection anxiety. Ideally, the safety device should provide an intermediate between a syringe or safety device (such as UltraSafe) and a full automatic injector.

SUMMARY OF THE INVENTION

In a first aspect of the invention there is disclosed a grip accessory for a manual injection device, the accessory comprising: a housing comprising a generally hollow body configured to support a manual injection device therein, the housing comprising: a distal portion comprising a first opening into which a manual injection device can be inserted; a proximal portion comprising a second opening through which a needle of the manual injection device extends, the proximal portion comprising a skin contacting surface at a proximal end of the device; and an intermediate portion extending between the proximal and distal portions. The skin contacting surface of the grip accessory device can serve to limit the depth of insertion of the needle of an injection device. For example, the grip accessory can be configured to limit the depth of needle insertion for subcutaneous, subdermal, intramuscular injection, etc.

In order to minimise the complexity of manufacturing and assembly of grip accessories according to the present invention, some embodiments of the grip accessory are preferably formed as a single piece, for example, by injection moulding or additive manufacturing process (e.g. 3D printing). In some embodiments of the present invention, the grip accessory comprises no moving parts.

In some embodiments, the distal portion may comprise two diametrically opposed tongues having cut-outs therebetween. The tongues can comprise gripping surfaces, for example, a ridged surface region, on their outer surfaces. The tongues may also comprise securing means on their inner surfaces for securing an injection device therebetween. In other embodiments, the distal portion may be a substantially tubular body (not limited to having a circular cross-section) that surrounds the distal end of the injection device.

Grip accessories according to the present invention may be provided with an injection device therein. The injection device can be a conventional syringe or it can be an injection safety device, for example an injection safety device can comprise a syringe housing for holding a syringe body; a safety shield movably mounted relative to the syringe housing between a retracted position in which the proximal end of the needle extends from the proximal end of the safety shield and an extended position, in which the safety shield extends over the proximal end of the needle; a biasing device for biasing the shield towards its extended position; and a releasable locking mechanism for holding the sleeve in its retracted position.

The grip accessory can be configured to support an injection device within the generally hollow body such that the proximal tip of a needle of the injection device extends a pre-determined distance, $D_1$, beyond the plane P defined by the skin contacting surface. The distance, $D_1$, can be in one or more of the following ranges: between 3 mm and 12 mm; between 4 mm and 10 mm; and between 5 mm and 8 mm. Preferably, the distance, $D_1$, is greater than a second distance, $D_2$, which is the shortest distance in the plane P between the needle and an outer edge of the proximal portion, preferably an outer edge of the flange. The distance $D_1$ may be less than the total distance, $D_3$, between the proximal end of the needle and the point at which the needle is connected to the syringe body.

In some embodiments, the support structure may secure a syringe within the housing, such that the needle extends from the plane P by a fixed distance $D_1$. In other embodiments, the support structure may secure a safety device within the housing. In these embodiments, the safety device is fixedly mounted within the housing such that in an injection ready state, the syringe extends from the plane P by a fixed distance $D_1$.

The support structure for supporting an injection device within the housing can comprise a recess for confining a flange of an injection device, such as a flange of a syringe or a flange of a safety device. Ramped surfaces may be provided distally of the recesses to guide the flanges of the injection device into the recesses. The housing may further comprise at least one rib, preferably extending longitudinally along an interior surface of the housing, to limit or prevent rotational and/or lateral movement of the manual injection device.

In some embodiments, the grip accessory can comprise a flange at the proximal end of the housing that at least partially surrounds the second opening and provides the skin contacting surface at the proximal end of the device. The flange may be formed as a flared opening, and extend radially outwardly from the housing. The flange may comprise a substantially circular footprint (the foot print being the cross-sectional area bounded by the outer circumference of the flange). Alternatively, the flange may have an elongate footprint, i.e. oval or rectangular. An oval footprint preferably comprises two opposing parallel lines joined by two circular arcs. By providing opposing parallel sides, the tendency for the device to roll on flat surfaces is eliminated. Of course, an elliptical oval footprint is also within the scope of the present invention. The flange can be helpful in limiting the angle of insertion of the needle. The flange can also help to further control the depth of insertion by increasing the surface area in contact with the skin and limiting the extent to which the skin contacting surface can be pressed into the injection site. The flange can have a minimum outer dimension (i.e. the shortest distance between two opposing outer edges of the flange) of at least 8 mm, more preferably at least 15 mm, and most preferably at least 25 mm.

An inner sheath can be provided at the proximal end of the housing. The inner sheath may be cylindrical and may have a narrow diameter relative to the outer diameter of the skin contacting surface. For example, the inner diameter of the sheath can be at least 8 mm. The inner sheath can provide at least two advantages. It can help to stabilise the proximal tip of the injection device by limiting lateral movement. It can also serve to restrict the size of the opening at the proximal end of the device to prevent a user inserting his or her finger into the housing after an injection has been completed, thereby avoiding needle stick injuries. Advantageously, the inner sheath also restricts the user's view into the proximal end of the device, thereby shielding the needle from view of the user to reduce injection anxiety.

In some embodiments, the aperture at the proximal end of the housing can have a minimum outer dimension of at least 12 mm, more preferably at least 15 mm, and most preferably at least 18 mm.

The skin contacting surface has an outer radius $R_1$ The radius $R_1$ can be chosen to help limit the depth of insertion of the needle. For example, the radius $R_1$ can be at least 6 mm; at least 8 mm; at least 9 mm. Preferably, the ratio of $R_1:D_1$ is: at least 1:1; at least 1.5:1; or at least 2:1. This helps to limit the depth of insertion of the needle to 90 degrees relative to the surface of the skin at the injection site.

The generally tubular hollow body for accommodating the injection device can comprise a substantially square or circular transverse cross-section. Alternatively, the housing, and in particular the intermediate portion, can comprise an elongate transverse cross-section. The transverse cross-section serves to orient the device comfortably in the user's palm when a first grip is used. The elongate cross-section also prevents the device from rolling on a flat surface. The transverse cross-section is the cross-section defined in a plane perpendicular to the longitudinal axis A of the housing, i.e. the axis along which the piston rod travels during injection of medicament.

In some embodiments, the intermediate portion of the grip accessory has an outer circumference that is less than the outer circumference of the proximal portion and/or the outer circumference of the distal portion, e.g. the flange. This narrower intermediate portion can aid orientation of the grip in the user's hand and prevent the user's hand protruding beyond the plane P, where it would alter the depth of injection achieved.

The change in the maximum outer dimension between the intermediate portion and the proximal portion can also provide a ledge or bearing surface that allows the device to be gripped in a conventional or dart grip.

The distal portion of the housing may comprise at least one indent for supporting a finger of the user.

The distal portion can comprise at least one aperture or cut-out adapted to provide viewing of at least a portion of the manual injection device. The apertures or cut-outs also reduce the extent of the rim on which the plunger can become caught towards the end of the injection. In preferred embodiments, the distal portion of the housing has an elongate transverse cross-section with the apertures or cut-outs provided on the elongate sides. This ensures that risk of the plunger becoming caught on the distal most edge of the 5 housing is reduced. The cut-out may also expose at least a portion of the bung of a syringe or a portion of a locking mechanism of a syringe safety device. This may allow the user to inspect the distal end of the syringe before injection to confirm that the syringe barrel is full.

In addition or as an alternative to the cut-out, the generally tubular housing may comprise at least one window to allow inspection of the syringe barrel. The window can be provided on the intermediate portion and extends along all or part of the barrel of a syringe mounted in the housing. Where the housing comprises an elongate transverse cross-section, a window is preferably provided on an elongate side of the housing. This ensures that when the device is settled in a user's palm, the window is usefully orientated. Preferably, two diametrically opposed windows are provided on opposite sides of the housing to allow for transmission of light and better visibility. The window along the body of the tubular housing can allow the user to inspect the drug prior to injection, to check the contents of the syringe for particles or discoloration of the drug.

The grip accessory according to the present invention can be dimensioned for one handed use. For example, the length of the intermediate portion can be in one or more of the following ranges: between 20 mm and 120 mm; between 30 mm and 100 mm; between 40 mm and 90 mm; and between 50 mm and 70 mm. The total length of the grip accessory, from the proximal end of the proximal portion to the distal end of the distal portion can be in one or more of the following ranges: between 40 mm and 120 mm; between 50 mm and 100 mm; between 60 mm and 110 mm; and between 70 mm and 100 mm.

In some embodiments, the manual injection device further comprises a plunger, the plunger comprising an actuation surface at the distal end of the plunger to which an actuation force can be applied for moving the plunger along the longitudinal axis to deliver the dose of medicament.

The plunger has a length, extending from its proximal to its distal end that may be between 50 mm and 100 mm, more preferably between 60 mm and 90 mm, and most preferably between 60 mm and 80 mm.

In some embodiments, the grip accessory at least partially surrounds the releasable locking mechanism. This prevents the user accidentally releasing the releasable locking mechanism as they handle the device.

The releasable locking mechanism can comprise at least one deflectable latching arm moveable from a first position in which it causes the safety shield to be retained in its retracted position, and a second position, in which it no longer retains the safety shield in its retracted position. The plunger can be configured to move the at least one flexible latch arm from its first position to its second position.

In some embodiments, the actuation surface moves the flexible latch arm from the first position to the second position. In other embodiments, the plunger can further comprise an unlatching portion proximal of the actuation surface configured to move the flexible latch arm to its second position.

The unlatching portion may comprise a disc or flange extending from the plunger rod proximal of the actuation surface, which may be integrally molded with the plunger rod.

In some embodiments, the distal portion of the housing may further comprise guide means for guiding the unlatching portion of the plunger to a position at which it unlatches the releasable locking mechanism.

The guide means can comprise a plurality of ribs extending longitudinally along an interior surface of the housing body that defines a channel for receiving the unlatching portion and prevents lateral movement of the unlatching portion.

At least one of the plurality of ribs can include a curved distal surface to guide the unlatching portion into the channel.

According to a second aspect of the invention, there is provided a grip accessory for a manual injection device, the grip accessory comprising: a housing comprising a generally hollow body for supporting a manual injection device therein, the housing comprising: a distal portion comprising a first opening into which a manual injection device can be inserted; a housing configured to support a manual injection device therein, the housing comprising: a proximal portion comprising a second opening through which a needle of the manual injection device is extendable, the proximal portion comprising a skin contacting surface at a proximal end of the device; an intermediate portion extending between the proximal and distal portions; and guide means on an interior surface of the distal portion for guiding a plunger rod of an injection device during delivery of an injection.

The guide means can comprise at least one longitudinal rib extending along an interior surface of the housing for limiting lateral movement of a plunger rod of the injection device. Preferably, the guide means comprises a plurality of longitudinal ribs. The ribs can extend proximally from the distal end of the housing. The plurality of ribs can define a channel within the distal portion of the housing along which the plunger rod travels.

In some embodiments, the plurality of ribs comprise a curved distal face to guide the plunger rod into the channel and prevent the plunger rod from catching on the distal end of the grip accessory. The distal face of the ribs may also be angled to achieve this goal. Preferably, the curved or angled ribs provide a flared opening to the channel to guide the unlatching surface into the channel.

The grip accessory may support an injection device such as a conventional syringe or a safety device therein. The safety device or manual injection device can comprise a syringe body having a needle at its proximal end; a syringe sheath supporting the syringe body therein; a safety shield movable relative to the syringe sheath between a retracted position, in which the needle extends from the proximal end of the safety shield, and an extended position, in which the safety shield extends over the needle; a biasing element for biasing the shield towards its extended position; a releasable locking mechanism for holding the syringe sheath in its retracted position against the bias of the biasing element, the releasable locking mechanism being movable from a first position in which it prevents movement of the syringe shield relative to the syringe sheath and a second position in which it does not prevent movement of the safety shield relative to the syringe sheath; and a plunger rod extending from the distal end of the syringe body for delivering a dose of medicament though the needle, wherein the plunger comprising an unlocking component for moving the releasable locking mechanism from its locked position to its unlocked position as the plunger rod is moved proximally to deliver a dose of medicament.

The releasable locking mechanism can comprise at least one deflectable latching arm moveable from a first position in which it causes the safety shield to be retained in its retracted position, and a second position, in which it no longer retains the safety shield in its retracted position; and the plunger comprises an unlatching element configured to move the at least one flexible latch arm from its first position to its second position. The releasable locking mechanism can be disposed within the channel formed by the plurality of ribs.

The unlatching element provided on the plunger can be a flange or disk extending from the plunger rod. Preferably, the channel is dimensioned to receive the unlatching element and prevent lateral movement of the unlatching element relative to the housing.

Additionally or alternatively, the plunger rod can comprise an actuation surface at its distal end for receiving a user's thumb or finger when delivering an injection and wherein the channel is dimensioned to receive the actuation surface and prevent lateral movement of the actuation surface relative to the housing.

In a third aspect of the invention, there is provided a manual injection device comprising: a syringe housing for holding a syringe body with a discharge nozzle; a safety shield movable between a retracted position and an extended position in which the safety shield extends over the needle; biasing device for biasing the safety shield to its extended position; a releasable locking mechanism for holding the safety shield in its retracted position when in a locked position, and allowing the safety shield to move to its extended position under the influence of the biasing device when in its unlocked position; and a plunger for delivering a dose of medicament through the discharge nozzle, the plunger being movable along a longitudinal axis from a distal position to a proximal position, wherein the plunger comprises: an actuation surface at the distal end of the plunger to which an actuation force can be applied for moving the plunger along the longitudinal axis to deliver the dose of medicament; and an unlatching element proximal of the actuation surface configured to unlock the releasable locking mechanism, thereby allowing the safety shield to move to its extended position.

The releasable locking mechanism can comprise at least one deflectable latching arm moveable from a first position in which it causes the safety shield to be retained in its retracted position, and a second position, in which it no longer retains the safety shield in its retracted position. The plunger can be configured to move the at least one flexible latch arm from its first position to its second position when it is moved from its distal position to its proximal position.

The unlatching element can be an annular projection, flange or disc extending from the body of the plunger and spaced from the actuation surface of the plunger.

In some embodiments the plunger can provide an unlatching surface at a change in dimension of the plunger rod. In this case, the plunger rod comprises a distal portion having a first cross-sectional diameter and a proximal portion having a second cross-sectional diameter. The first cross-sectional diameter can be greater than the second cross-sectional diameter. At the point at which the proximal portion meets the distal portion, a bearing surface is provided that can act as an unlatching surface to move the releasable locking mechanism to its second position.

In both cases, the unlatching portion can comprise a curved proximal surface or a flat proximal surface.

In any of the grip accessories in accordance with the present invention, a retractable sheath can be provided at the proximal end of the device, which is movable between an extended position in which the sheath extends over the proximal end of the discharge nozzle and a retracted position, in which the discharge needle from the retractable sheath. Preferably, the retractable sheath is retractable to a position in which its proximal end does not extend from the plane P defined by the skin contacting surface.

BRIEF DESCRIPTION OF THE DRAWINGS

The above mentioned and other features and advantages of the present invention will be better understood by reference to the following description of exemplary embodiments of the present invention, taken in conjunction with the accompanying drawings, where:

FIG. 3 shows the proximal end of a grip accessory according to one embodiment of the present invention.

FIG. 4 shows a grip accessory according to an exemplary embodiment of the present invention, housing the injection device of FIG. 1.

DETAILED DESCRIPTION

Figure 1A:
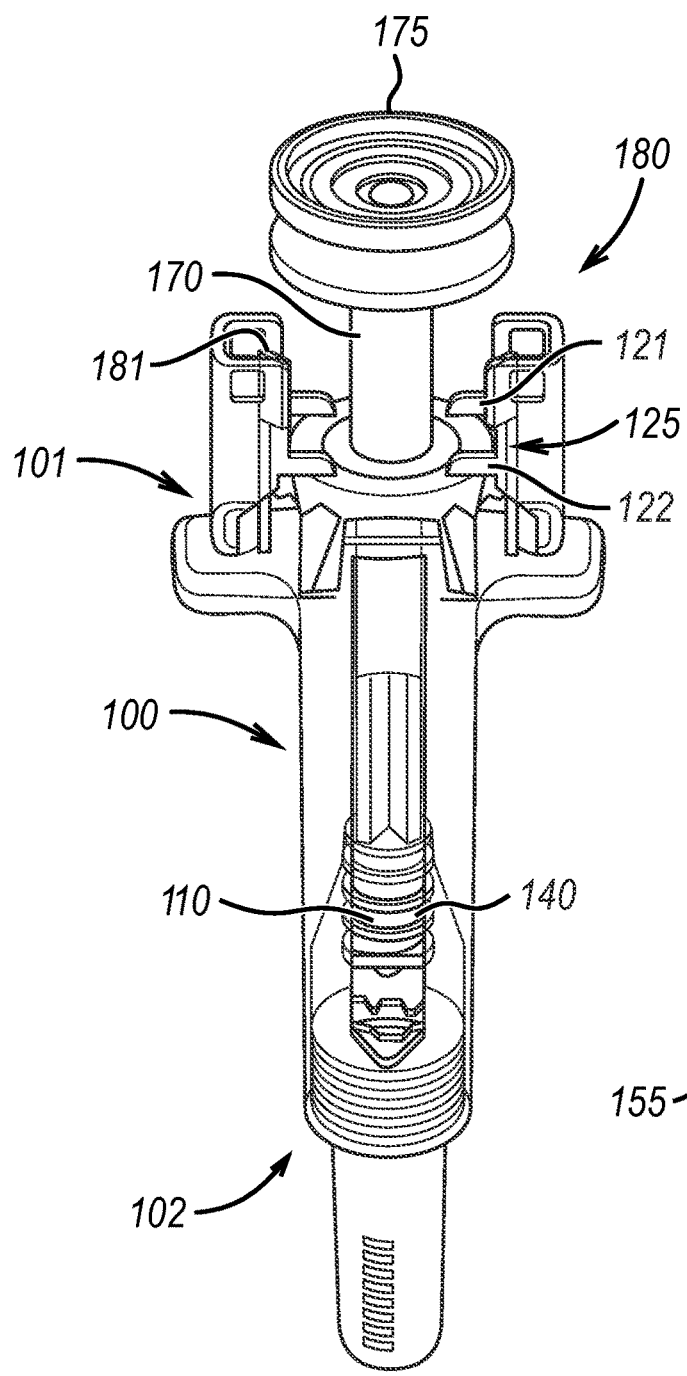
FIGS. 1A-B show an UltraSafe injection device in an injection ready state (FIG. 1A, and a safe, post-injection state (FIG. 1B).
Figure 1B:
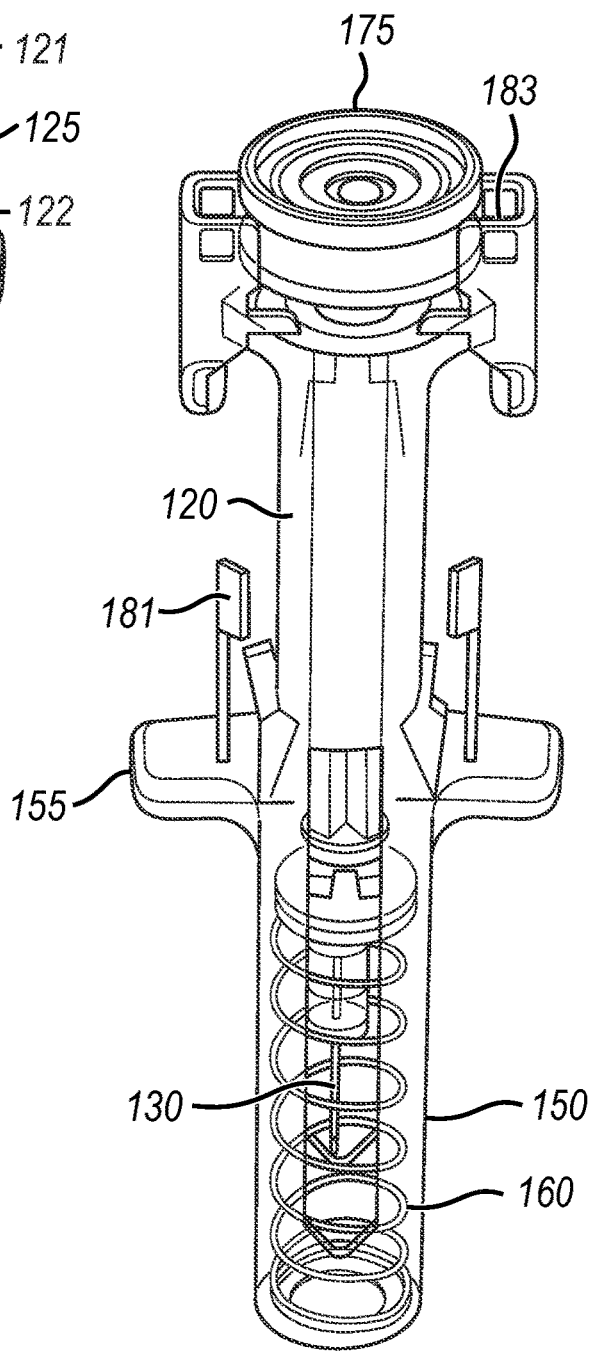
Figure 2B:
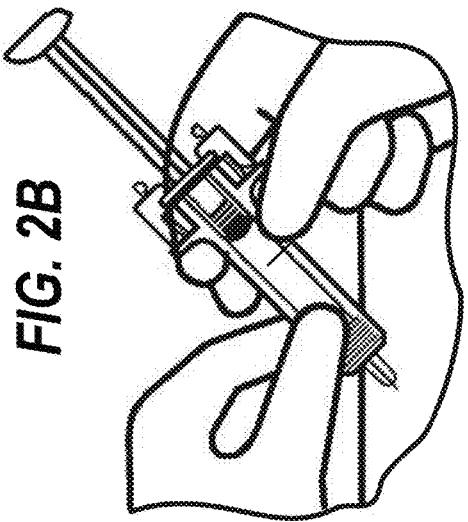
FIGS. 2A-D shows the typical instructions for use of the injection device of FIG. 1.
Figure 2D:
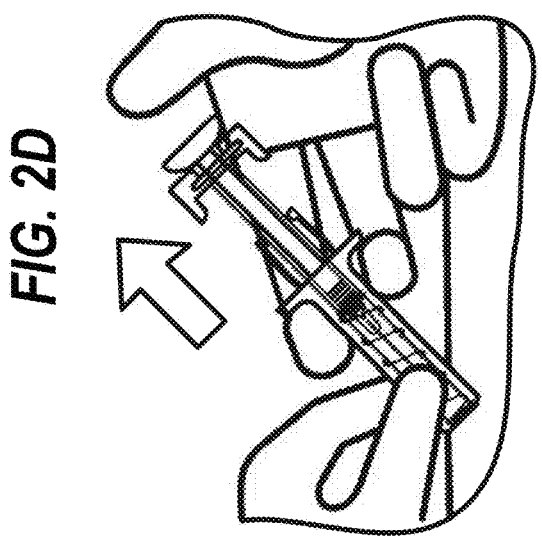
Figure 2A:
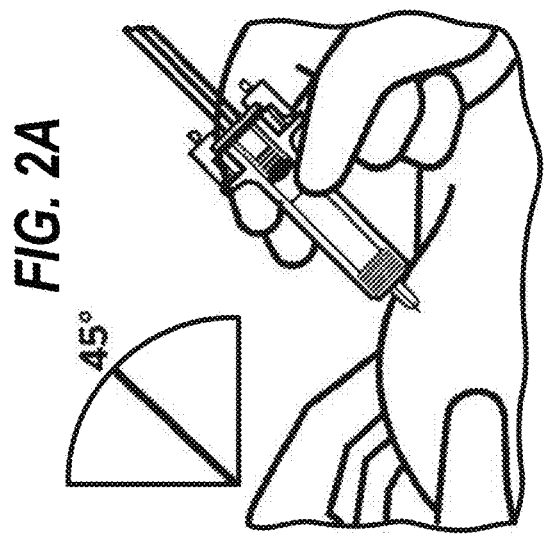
Figure 2C:
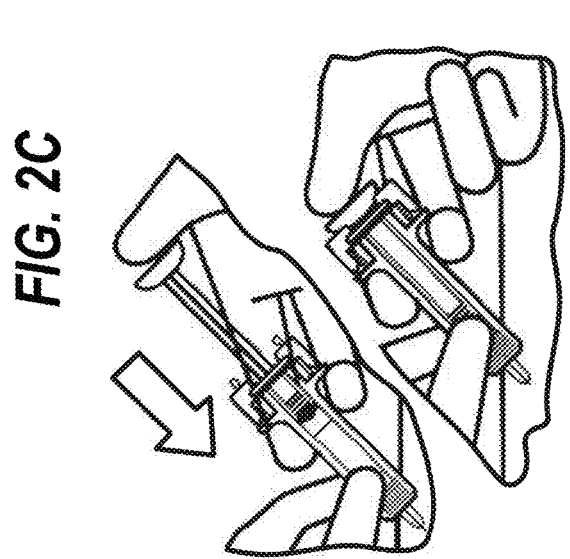

FIGS. 1A-B show a manual injection device 100 that is suitable for use with a grip accessory according to the present invention. The injection device 100 comprises a syringe 110, which extends from a proximal end comprising a needle 130, to an open distal end. The open distal end of the syringe is sealed by a bung 140. A needle cap 190 is optionally provided to sheath the needle 130.

The syringe 110 is secured within a syringe sheath 120 by a syringe locking element 125. The syringe locking element 125 may comprise diametrically opposed abutment surfaces 121, 122 between which the flange of a standard syringe is confined. The confinement of the flanges between abutment surfaces 121, 122 prevents movement of the syringe 110 relative to the syringe sheath 120.

The syringe sheath 120 comprises an open distal end 101, into which the syringe 110 can be inserted, and an open proximal end 102, from which the needle 130 extends when the syringe 110 is secured within the sheath 120. A safety shield 150 is movably mounted with respect to the syringe sheath 120. The safety shield 150 is movable between a retracted position (shown in FIG. 1A), in which the needle 130 extends beyond the proximal end of the safety shield, and an extended position (shown in FIG. 1B), in which the safety shield extends beyond the proximal end the needle. In the second position shown in FIG. 1B, the needle 130 is covered by the safety shield 150, thereby shielding the user from the needle and preventing accidental needle-stick injuries.

To allow the user to grip the injection device 100 with a conventional dart grip (as shown in FIG. 2), the safety shield 150 comprises flanges 155 at or towards its distal end. The flanges 155 shown in FIG. 1 extend from the safety shield 150. However, the skilled person will appreciate that the flanges 155 can be provided on the syringe sheath 120.

The safety shield 150 is biased into its extended position relative to the syringe sheath 120 (shown in FIG. 1B) by a biasing element 160. The biasing element 160 shown in FIGS. 1A-B takes the form of a coil spring arranged between the syringe sheath 120 and the safety shield 150 such that the safety shield 150 is biased proximally relative to the syringe sheath 120 into its extended position.

A releasable locking mechanism 180 retains the safety shield 150 in its retracted position relative to the syringe sheath 120. The locking mechanism 180 is movable between a locked position, in which the locking mechanism 180 prevents the safety shield 150 moving relative to the syringe sheath 120 (FIG. 1A), and an unlocked position in which the locking mechanism 180 no longer prevents movement of the safety shield 150 relative to the syringe sheath 120. Once the locking mechanism is moved to its unlocked position, the safety shield 150 moves to its extended position under the influence of the coil spring 160 (FIG. 1B).

In the device shown in FIGS. 1A-B, the locking mechanism 180 between the safety shield 150 and the syringe sheath 120 takes the form of a pair of flexible latch arms 181 provided on the safety shield 150, which engage opposing latching surfaces 183 on the syringe sheath 120. The flexible latch arms 181 are biased into a first position in which they engage their respective latching surfaces 183, thus preventing proximal movement of the safety shield 150 relative to the syringe sheath 120. When the flexible latch arms 181 are moved against this bias, the latch arms 181 disengage their respective latching surfaces 183, thus permitting proximal movement of the safety shield 150 relative to the syringe sheath 120.

The latch arms 181 are configured to be moved from the first position to the second position by a custom plunger rod 170. The plunger rod 170 comprises an elongate member, configured at its proximal end to engage the bung 140 and move the bung proximally along the longitudinal axis of the syringe body to deliver a dose of medicament through the needle 130. At or towards its distal end, the plunger 170 is provided with an actuation surface 175 on which the user can place a thumb or finger to drive the plunger proximally to deliver the injection. As the plunger rod nears or reaches the end of its travel within the syringe body, the actuation surface 175 of the plunger rod 170 deflects the flexible latch arms 181 outwardly, to a position in which they no longer engage the latching surfaces 183 on the syringe sheath 120. The locking mechanism is thus released at the end of the injection and the safety shield 150 moves to its extended position.

Although not visible in the accompanying drawings, the manual injection device of FIGS. 1A-B can additionally comprise a safety lock for locking the safety shield 150 in its extended position after the injection has been completed.

A grip accessory for use with the injection device of FIGS. 1 and 2 will now be described with reference to FIGS. 3 to 7.

As shown in FIG. 3, the grip accessory 300 comprises a housing 310 having a generally hollow body for accommodating injection device 100. The injection device 100 is supported in the housing such that the needle 130 extends a predetermined distance, $D_1$, beyond a skin contacting surface that surrounds an aperture at the proximal end of the housing. During an injection, the maximum depth of insertion of the needle is limited by the skin contacting surface 367 coming into contact with the injection site. This helps to control the depth of insertion of the needle without the needle to pinch the skin (as shown in FIG. 2) and insert the needle at a 45 degree angle relative to the injection site. Instead, the needle can be inserted at an angle of 90 degrees to the full extent permitted by the grip accessory. The extent to which the needle extends from the plane P defined by the skin contacting surface can be selected depending on the type of injection required (subcutaneous, intramuscular, etc.). For example, for subcutaneous injection, the distance $D_1$ may be between 3 mm and 12 mm, more preferably between 4 mm and 10 mm and more preferably between 5 mm and 8 mm.

The grip accessory of the present invention can take various forms. As shown in FIG. 4, a grip accessory 300 comprises a housing 310, having a distal portion 330, a proximal portion 320 and an intermediate portion 340 extending between the proximal and distal portions. The distal portion 330 of the housing 310 comprises a distal opening 335 to allow insertion of the injection device into the generally hollow body. Proximal of the distal opening, the housing 310 comprises two recesses 352 that confine the flanges 155 of the safety shield 150 and secure the injection device 100 within the housing. With the flanges 155 confined in recesses 352, the syringe 110 and needle 130 are fixed relative to the grip accessory 300 until locking mechanism 180 is released.

To facilitate insertion of the injection device 100 into the housing 310, ramped surfaces (not shown) may be provided on an interior of the housing 310 immediately distal of the recesses 352, which guide the flanges 155 of the injection device 100 into the recesses 352. Once the flanges 155 ride over ramps (not shown) and snap into recesses 352, the injection device 100 is locked into the grip accessory 300. In some embodiments, although not all, the housing further comprises ribs on the interior of the housing, for preventing lateral and rotational movement of the injection device 100 within the housing 310.

As shown in FIG. 4, the distal portion 330 of the housing 310 can at least partially surround the locking mechanism 180 of the injection device 100 to provide a shield around the locking mechanism 180 of the injection device 100. The shield prevents the user's hand from coming into direct contact with the locking mechanism 180 and inadvertently moving the releasing locking mechanism 180 and activating the needle shield before the injection is complete. To allow the user to view the distal end of the injection device 100, the distal portion 330 may comprise one or more cut-outs 380. By providing cut-outs 380 at the distal end of the housing, the risk of the plunger becoming caught at the distal end of the housing is minimized. To further mitigate this risk, the plunger may comprises a flexible unlatching component that can flex upon contact with the relatively rigid housing. This will be described in more detail below.

In some embodiments, the housing 310 also comprises at least one, and preferably two or more indentations 385 to provide improved grip for the user's fingers. As shown in FIG. 3, the indentations 385 can be provided at or near the junction of distal portion 330 and the intermediate portion 340. The indentions 385 may provide bearing surfaces 387 for the user's fingers, which can be used to facilitate conventional dart grip of the accessory 300 (see FIG. 2). Alternatively, the indentations 385 can be provided on the distal portion 330. In either case, the indentations 385 facilitate correct and comfortable placement of the user's fingers when the device is used with a first grip (with the grip accessory placed in the palm of the user's hand and the thumb positioned to actuate the plunger rod 170) or provide a bearing surface for a convention dart grip (shown in FIG. 2).

The intermediate portion 340 extends between the proximal portion 320 and the distal portion 330 of the housing. The intermediate portion 340 is preferably narrower than the proximal portion 320 and the distal portion 330. It has a generally tubular form that surrounds substantially all if the syringe sheath 120 and the safety shield 150 of the injection device (before the safety shield 150 is extended). The narrower intermediate portion 340 helps the user to grip the device when a first grip is used. It may also provide bearing surfaces for a dart grip, as described above.

The generally hollow housing 310 of the grip accessory can take various forms. In some embodiments, as shown in FIG. 4, the housing 310 has a generally elongate transverse cross-section, the transverse cross-section being defined in a plane perpendicular to the longitudinal axis A of the housing, i.e. the axis along which the piston rod travels during injection of medicament. The elongate transverse cross-section may be an ellipse, an oval, a rectangle or any other elongate shape. Advantageously, the elongate transverse cross-section allows the grip accessory to settle comfortably in the user's palm (when a first grip is used).

In some embodiments, as shown in FIG. 4, the intermediate portion 340 of the housing 310 comprises a window 395. The window 395 may be located on a long side of the housing 310 (defined as the long side of the elongate cross-section described above). Since the cross-section of the intermediate portion is elongate, the grip accessory naturally settles in the user's palm with the window 395 facing outwardly. Two windows 395 may be provided, one on each side of the housing 310.

In some embodiments, referring still to FIG. 4, the proximal portion 320 of the housing 310 comprises a flared opening that provides a flange 365 surrounding the proximal opening 360. The flange 365 provides the skin contacting surface 367 that is placed against the skin at the injection site to control the depth of insertion of the needle 130. The flange 365 also prevents the user from inadvertently placing their fingers between the grip accessory and the injection site, which could limit or entirely prevent adequate insertion of the needle into the injection site.

The outer radius of the skin contacting surface can be chosen to help limit the angle of insertion of the needle 130. For example, the outer radius $R_1$ of the skin contacting surface 367 may approach or exceed the length of the needle $D_1$ that extends from the housing. Preferably, the minimum outer radius $R_1$ is at least 3 mm, more preferably at least 5 mm and more preferably at least 8 mm.

In addition to the above, the flange 365 may advantageously increase the surface area of the housing in contact with the injection site, thereby reducing pressure and increasing the comfort for the user. The increased surface area of the flange also helps the user to place the proximal end of the device flat (with the needle at 90 degrees) against the injection site. However, the skilled person will recognize that the flange 365 is not essential. Embodiments of a grip accessory in accordance with the present invention that do not comprise a flange 365 will be described in more detail below with reference to FIGS. 6A-D.

In some embodiments, as shown in FIG. 4, an inner sheath 370 can be provided within the circumference of the flange 365. The inner sheath 370 effectively reduces the diameter of the proximal opening 360 through which the needle 130 of the injection device 100 extends. The sheath 370 provides several advantages. The sheath 370 supports the syringe against radial lateral movement, thereby improving the stability of the syringe within the device. It may also help to prevent needle stick injuries after completion of the injection device because the reduced diameter of the proximal opening 360 is sized to prevent a finger being inserted into the housing 310. The reduced diameter of the inner sheath also restricts the visibility of the needle and helps to reduce injection anxiety in the substantial portion of the population that is needle phobic. Finally, the sheath 370 can reduce skin bulging at the injection site into the proximal end of the device. Since skin bulge impacts the total depth of insertion of the needle, this can provide a significant advantage in some embodiments. Preferably, the inner sheath 370 does not extend beyond the plane defined by the skin contacting surface of the housing 310.

In some (although not all) embodiments, referring in particular to FIG. 4, the grip accessory may be provided with a modified plunger 270. The modified plunger 270 may comprise an actuation surface 275 for receiving a user's thumb or finger to deliver the injection and an unlocking component 280, proximal of and spaced from the actuation surface 275, for unlocking the releasable locking mechanism 180 of the injection device 100. The unlocking component 280 unlocks the releasable locking mechanism 180 in a similar manner to the actuation surface 175 described above, by deflecting the latch arms 181 away from their rest position, in which they engage the latching surfaces 183 on the syringe sheath 120. The unlocking component can take the form of a disk 280 that extends around the plunger rod, proximal of the actuation surface 275. Preferably, the disk 280 is formed of a flexible material that is more flexible than the main housing of the grip accessory. This allows the disk 280 to flex in the event that the plunger comes into contact with the grip accessory housing whilst slightly misaligned during injection, thereby preventing the plunger becoming caught on the grip accessory housing before the injection has been completed. The skilled person will appreciate that a relatively flexible disk 280 can be provided in a number of ways. For example, the disk can be made of the same material as the grip accessory housing, but have increased flexibility by virtue of reduced thickness (relative to the grip accessory housing). The disk 280 may also be made from a material having a lower Young's modulus, i.e. an inherently more flexible material.

An advantage of the modified plunger 270 is that the actuation surface does not need to be brought into contact with the locking mechanism 180 to release the safety shield 150. Instead, the unlocking component 280 reaches the locking mechanism 180 to release the safety shield 150 due to its proximal location relative to the actuation surface. This means that the user's thumb/finger does not need to be brought into immediate proximity to the locking mechanism, thereby reducing the risk of the user's hand interfering with the locking mechanism and reducing the dexterity required to use the device. Preferably, the distance between the actuation surface and the proximal surface of the unlocking component is: at least 5 mm, at least 8 mm, at least 10 mm or at least 15 mm.

Of course, the skilled person will appreciate that the modified plunger shown in FIG. 3 is one of many modifications to the plunger rod that can be made to achieve the above effect. For example, instead of using an actuation surface 275 and disk-like unlocking component 280, the modified plunger may instead comprise a single component comprising an actuation surface at one end and an unlocking component at the other. In some embodiments, the unlocking component 280 may comprise a curved or beveled proximal surface for deflecting the latch arms 181, as described above.

Figure 5C:
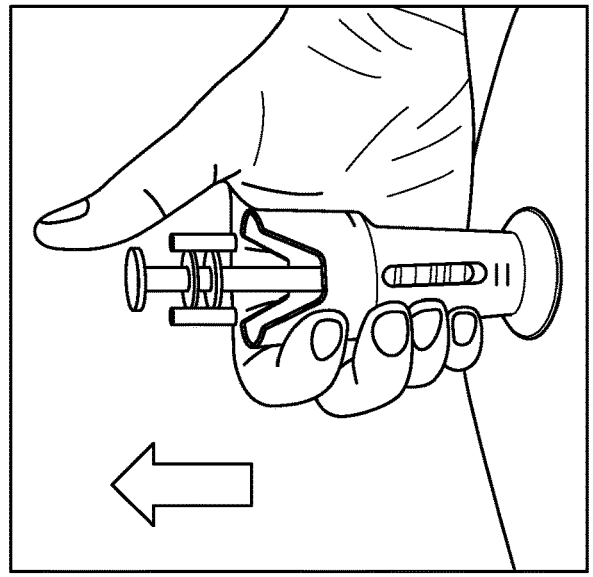
FIGS. 5A-C shows the grip accessory of FIG. 4 in use.
Figure 5B:
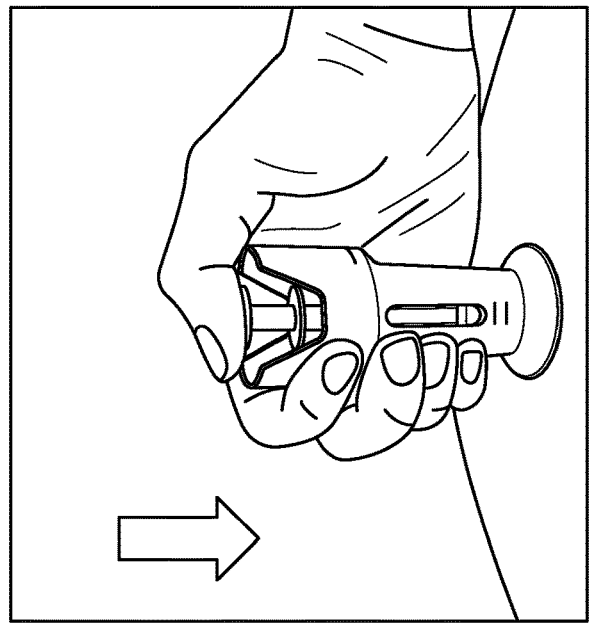
Figure 5A:
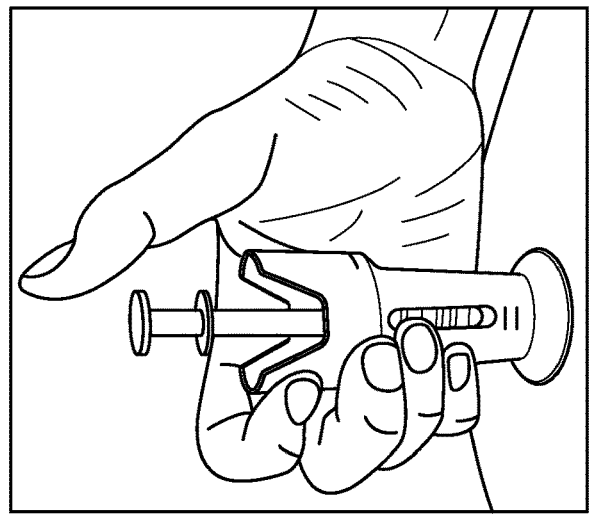

Use of the grip accessory 300 will now be described with reference to FIG. 5. In use the grip accessory 300 housing an injection device 100 is grasped by the user either in a dart grip or a first grip. The steps shown in FIG. 5 show a first grip, with the grip accessory 300 placed in the palm of the user. However, the skilled person will understand that a dart grip (as shown in FIG. 2) may also be used. The needle cap 190 is removed from the needle and the device is now ready for injection. The user places the grip accessory 300 against an injection site 10, with the needle at an angle of 90 degrees relative to the surface of the skin at the injection site 10 (see step (A) of FIG. 5). With the injection device placed against the injection site in this manner, the depth of insertion of the needle is controlled, as described above. Once pressed against the site, the user then depresses the plunger 170 (see step (B) of FIG. 5). The plunger 170 drives the bung 140 towards the proximal end of the injection device, thereby delivering a dose of medicament through the needle 130. When the plunger 170 reaches the end of its travel within the syringe 110 (i.e. when the bung 140 reaches the proximal end of the syringe and can travel no further) the unlocking component 180 disengages the latch arms 181 from the corresponding engagement surfaces 183, thereby allowing the safety shield 150 to advance relative to the syringe sheath 120 under the influence of the coil spring 160. Because the safety shield is locked in place within the grip accessory 300 (by virtue of flanges 155 confined in recess 352), the syringe sheath 120 and the syringe are retracted within the grip accessory 300 (see step (C) of FIG. 5). The grip accessory is now safe to remove from the injection site 10, with the needle shielded within the housing 310 of the grip accessory.

Figure 6A:
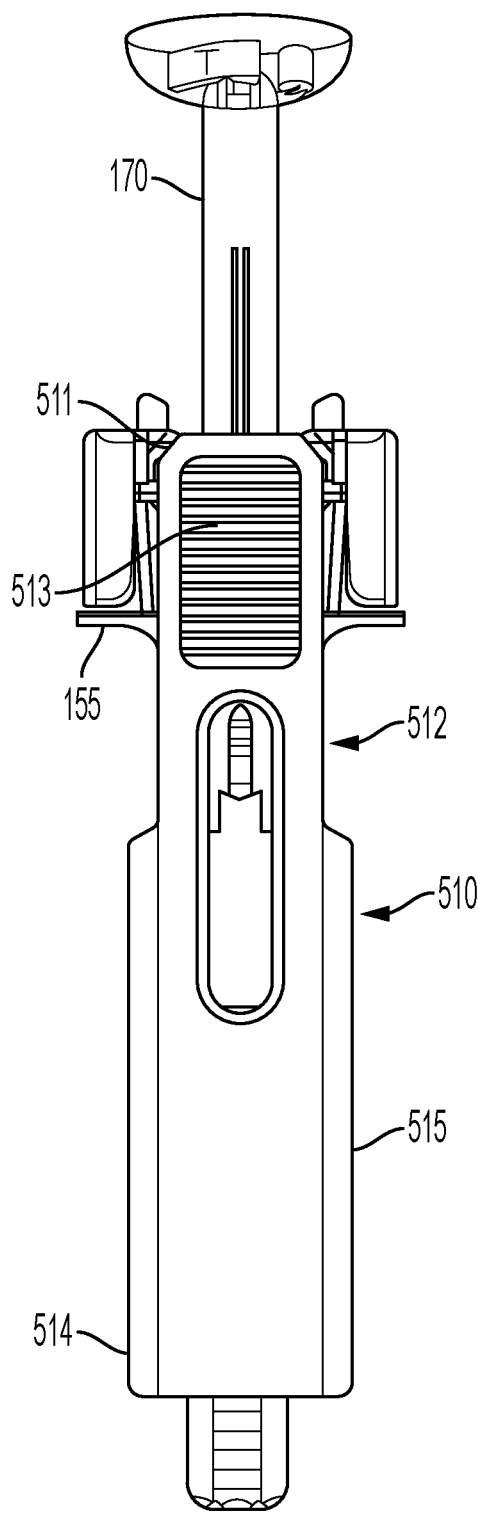
FIGS. 6A-D show alternative embodiments of a grip accessory according to the present invention.

FIGS. 6A-D show alternative embodiments of grip accessories according to the present invention. As shown in FIG. 6A, the distal portion 511 of the grip accessory may comprise opposing sidewalls, with cutouts 512 therebetween. In this embodiment the flanges 155 of the injection device 110 extend through the cutouts 512 such that the user can grip the injection device 110 directly. The embodiment shown in FIG. 6A also includes a ridged area 513 on an outer surface of the distal portion 511 to improve the user's grip on the device. The proximal end 514 of the embodiment shown in FIG. 6A does not include a flared proximal end. Instead, the intermediate portion 515 and the proximal portion 514 have substantially the same transverse cross-section.

The embodiment shown in FIG. 6A is intended for use with a conventional dart grip. Since the embodiment shown in FIG. 6A is not intended to be used in a first grip, the housing 510 does not comprise an elongate cross-section to help settle the device in a user's palm. Instead, the embodiment shown in FIG. 5A comprises a substantially square transverse cross-section (with rounded corners).

Figure 6B:
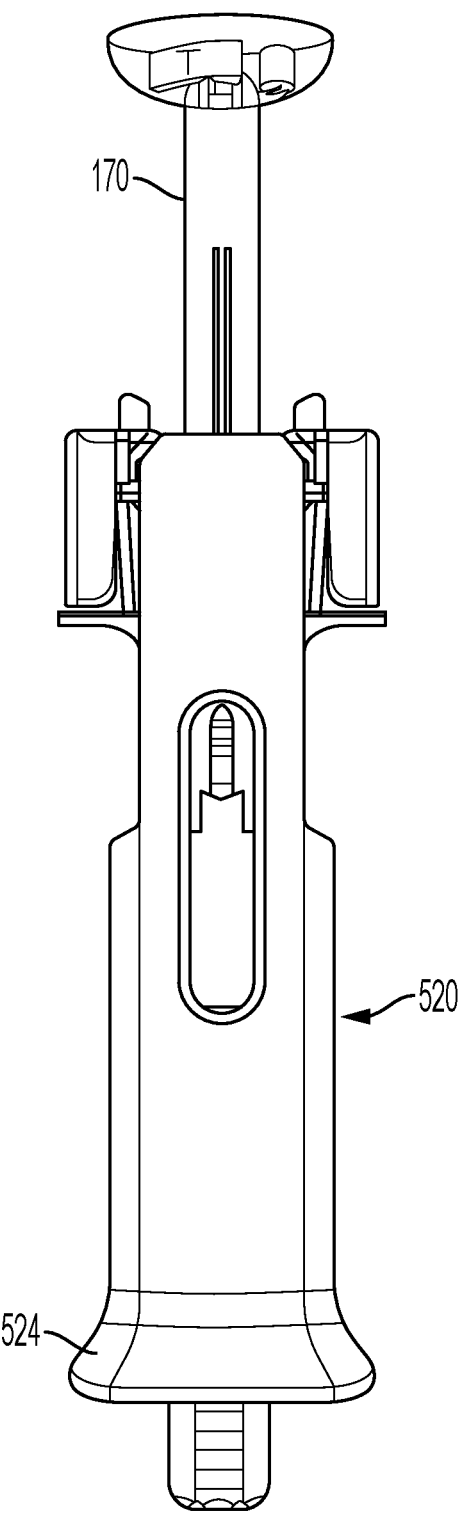

The embodiment shown in FIG. 6B is generally similar to the embodiment described above with reference to FIG. 6A, except for the addition of a flared proximal end 524. The ridged surfaces on the distal portion are also omitted from this embodiment.

Figure 6C:
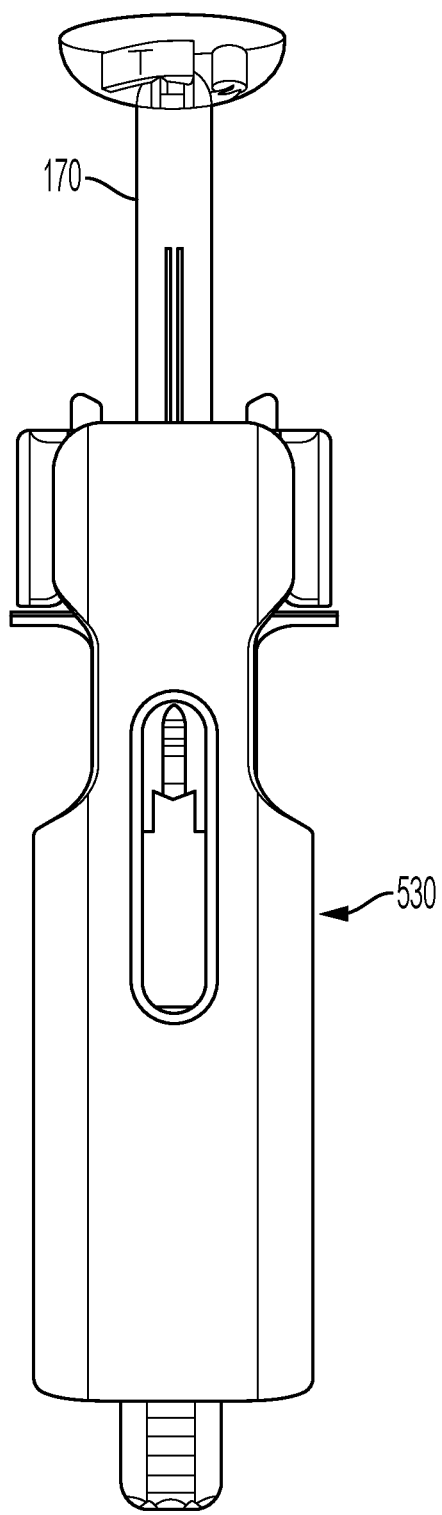

The embodiment shown in FIG. 6C is also generally similar to the embodiment described above with reference to FIG. 6A, except that the transverse cross-section of the housing 530 is elongate.

Figure 6D:
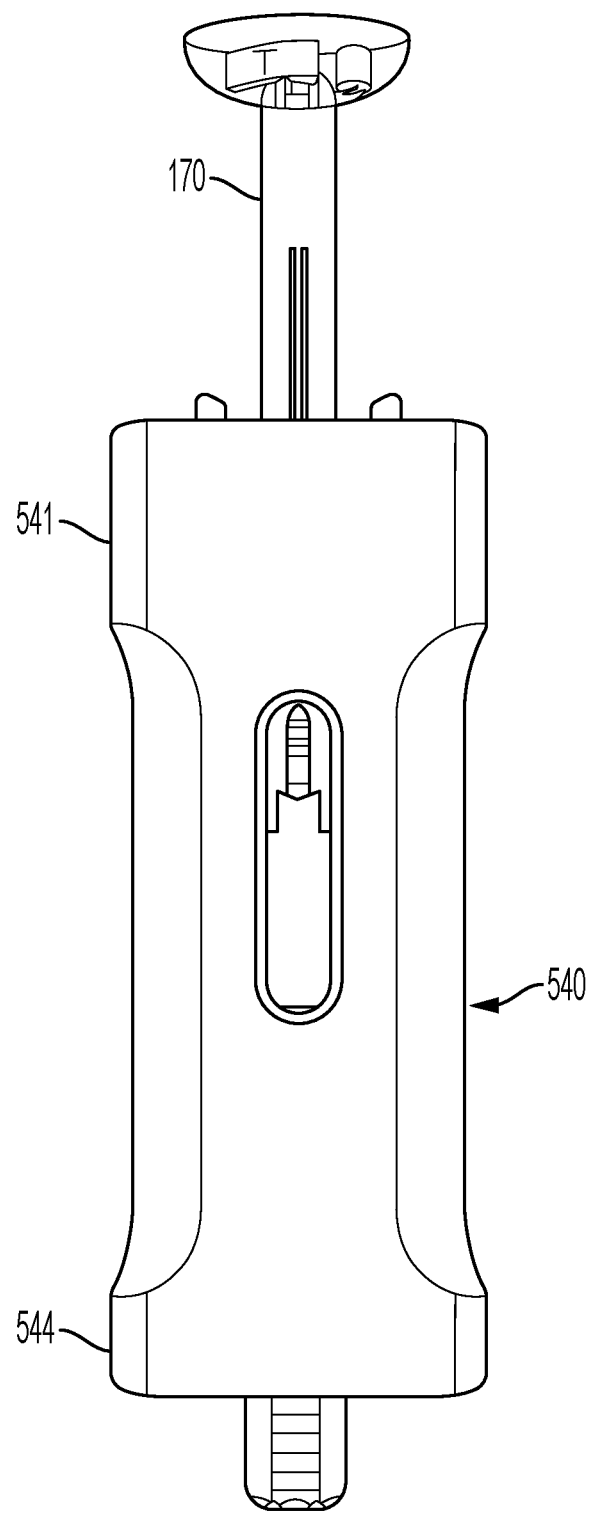

The embodiment shown in FIG. 6D is generally similar to the embodiment shown in FIG. 3, except that the distal end 541 of the housing 540 does not comprise cut outs, such as cut-outs 335 shown in FIG. 3. Instead, the distal portion 541 of the housing surrounds the locking mechanism 180 of the injection device 110, to minimize the risk of the user inadvertently disengaging the latch arms 181 from the latching surfaces 183 with their hand. The embodiment shown in FIG. 6D also shows an alternative to the flared end 365 shown in the embodiment of FIG. 3. Instead of a flared opening as shown in FIG. 3, the housing 540 of FIG. 6D has a generally tubular profile, with a narrower intermediate portion. This design may be particularly suited to embodiments that do not comprise an additional unlocking component 280 (as described above) and instead rely on the actuation surface 275 to unlock the releasable locking mechanism.

Figure 7:
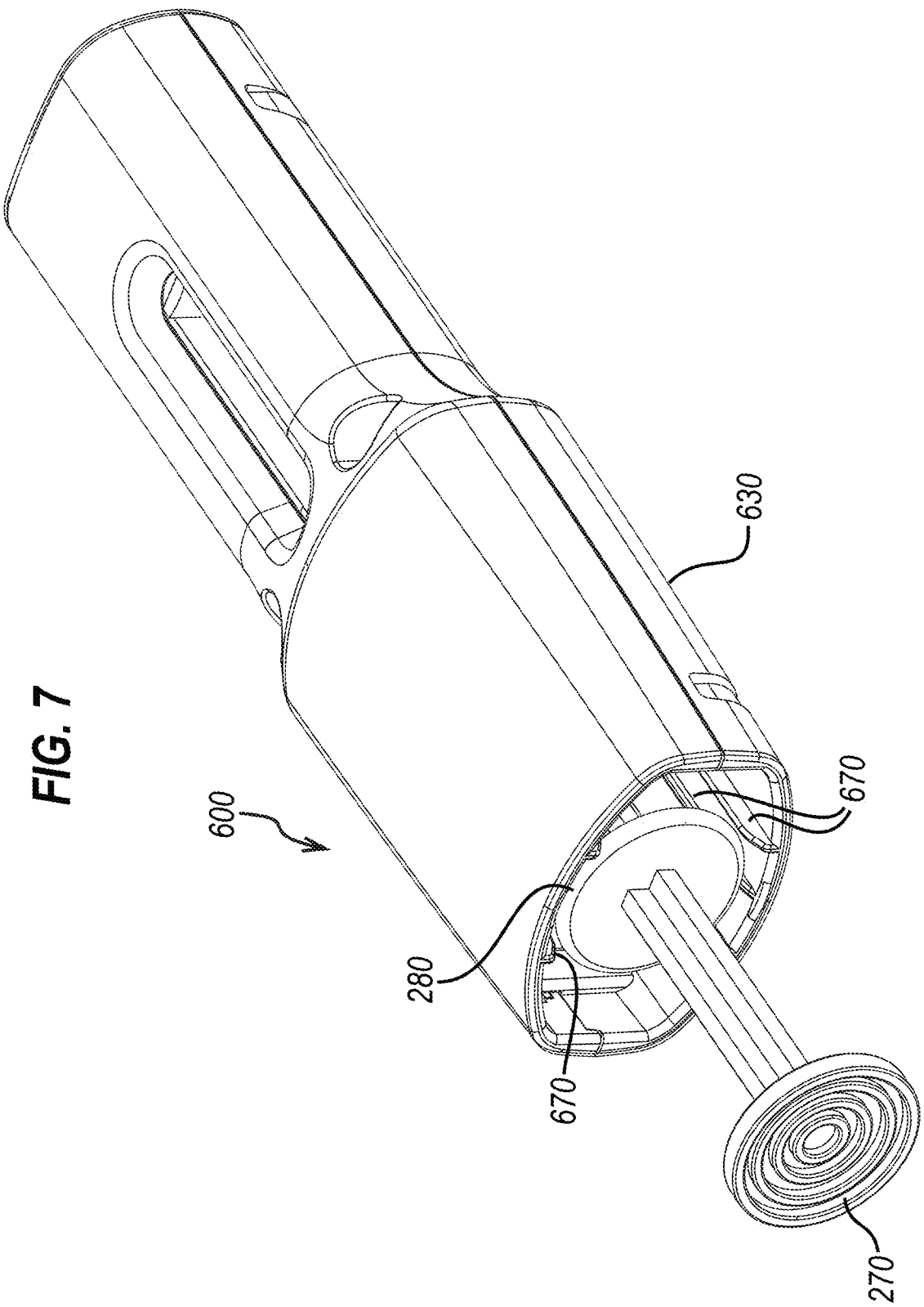
FIG. 7 shows another embodiment of a grip accessory according to the present invention.

Yet another embodiment of a grip accessory 600 in accordance with the present invention is shown in FIG. 7. In this embodiment, the distal portion 630 of the housing is extended to provide a grip portion at the distal end 630 of the grip accessory, rather than at the intermediate portion. This design allows one-handed, fist-grip use of longer injection devices, since the extended proximal portion 360 can be gripped in a user's palm without compromising the locking mechanism 180 of the injection device 110.

The embodiment shown in FIG. 7 also advantageously comprises plunger rod guide means 670 for guiding the plunger rod 170 in its travel along the longitudinal axis of the injection device. The plunger rod guide comprises a series of ribs 670 that prevent lateral movement of the unlocking component 280 relative to the housing. This ensures alignment of the unlocking component 280 with the latch arms 181 and prevents failure of the unlocking mechanism 180 due to the unlocking component 280 becoming caught on the housing or other parts of the locking mechanism.

Grip accessories according to the present invention are generally designed for one handed use, either in a conventional dart grip or a first grip, and are sized accordingly. For example, the total length of the grip accessory 300 (from the skin contacting surface to the distal end of the distal portion) is preferably in one or more of the following ranges: between 40 mm and 120 mm, between 50 mm and 100 mm, between 60 mm and 110 mm and between 70 mm and 100 mm. The intermediate portion of the grip accessory preferably has a total length in one or more of the following ranges: between 20 mm and 120 mm, between 30 mm and 90 mm and between 50 mm and 70 mm. So that the plunger can be operated whilst holding the device in one hand, the plunger preferably has a total length in one or more of the following ranges: between 50 mm and 100 mm, between 60 mm and 90 mm and between 60 mm and 80 mm.

Once appraised of the present disclosure, one skilled in the art will recognize that the grip accessory of the present invention may be modified to accommodate various different injection devices. While preferred embodiments of the present invention have been shown and described herein, it will be apparent to one skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

The invention claimed is:

1. A grip accessory for a manual injection device, the manual injection device comprising a plunger having a plunger rod and an unlocking body, the unlocking body having an unlocking surface movable with the plunger rod to unlatch at least one moveable latch of the manual injection device, the grip accessory comprising:
   a housing comprising a generally hollow body for supporting a manual injection device therein, the housing comprising:
      a distal portion comprising a first opening adapted to receive a manual injection device;
      a proximal portion comprising a second opening through which a needle of the manual injection device is extendable, the proximal portion comprising a skin contacting surface at a proximal end of the housing;
      an intermediate portion extending between the proximal and distal portions; and
      a guide on an interior surface of the distal portion, the guide configured to guide movement of the unlocking body of the plunger of the manual injection device towards the at least one movable latch as the unlocking body moves with the plunger rod during delivery of an injection.

2. The grip accessory of claim 1, wherein the guide comprises at least one longitudinal rib extending along an interior surface of the housing for limiting lateral movement of the unlocking body of the plunger of the manual injection device.

3. The grip accessory of claim 2, wherein the at least one longitudinal rib defines a channel within the distal portion of the housing along which the plunger travels.

4. The grip accessory of claim 2, wherein the at least one longitudinal rib comprises a curved distal face.

5. The grip accessory of claim 3, wherein the at least one longitudinal rib defines a flared opening to the channel to guide the unlocking body into the channel.

6. An injection device comprising:
the grip accessory of claim 1; and
a manual injection device comprising:
a syringe body having a needle at its proximal end;
a syringe sheath supporting the syringe body therein;
a safety shield movable relative to the syringe sheath between a retracted position, in which the needle extends from the proximal end of the safety shield, and an extended position, in which the safety shield extends over the needle;
a biasing element for biasing the shield towards its extended position;
the at least one movable latch, wherein the at least one movable latch is configured to hold the syringe sheath in its retracted position against the bias of the biasing element, the unmovable latch being movable from a locked position in which it prevents movement of the syringe shield relative to the syringe sheath to an unlocked position in which it does not prevent movement of the safety shield relative to the syringe sheath; and
the plunger, wherein the plunger extends from the distal end of the syringe body for delivering a dose of medicament through the needle, and the plunger comprises the unlocking body for moving the at least one movable latch from its locked position to its unlocked position as the plunger is moved proximally to deliver a dose of medicament.

7. The injection device of claim 6, wherein:
the at least one movable latch comprises at least one deflectable latching arm moveable from a first position in which it causes the safety shield to be retained in its retracted position, and a second position, in which it no longer retains the safety shield in its retracted position; and
the unlocking body is configured to move the at least one flexible latch arm from its first position to its second position.

8. The injection device of claim 6, wherein the unlocking body comprises a flange or disk extending from the plunger rod.

9. The injection device of claim 6, wherein wherein the guide comprises at least one longitudinal rib extending along an interior surface of the housing, the at least one longitudinal rib defining a channel that is dimensioned to receive the unlocking body and prevent lateral movement of the unlocking body relative to the housing.

10. The injection device of claim 9, wherein the plunger rod comprises an actuation surface at its distal end for receiving a user's thumb or finger when delivering an injection and wherein the channel is dimensioned to receive the actuation surface and prevent lateral movement of the actuation surface relative to the housing.

11. An injection device, comprising:
a manual injection device comprising:
a syringe housing adapted to hold a syringe body with a discharge nozzle;
a safety shield movable between a retracted position and an extended position, wherein the safety shield extends over the discharge nozzle when in the extended position;
a biasing device adapted to bias the safety shield to its extended position;
at least one movable latch adapted to hold the safety shield in its retracted position when in a locked position, and adapted to allow the safety shield to move to its extended position under the influence of the biasing device when in its unlocked position; and
a plunger adapted to deliver a dose of medicament through the discharge nozzle, the plunger being movable along a longitudinal axis from a distal position to a proximal position to deliver the dose of medicament, wherein the plunger comprises:
an actuation surface at the distal end of the plunger to which an actuation force can be applied for moving the plunger along the longitudinal axis to deliver the dose of medicament; and
an unlocking body proximal of the actuation surface and having an unlocking surface configured to unlock the at least one movable latch to allow the safety shield to move to its extended position when the unlocking body is moved proximally into engagement with the at least one movable latch, wherein the actuation surface has a cross-sectional dimension that is greater than a cross-sectional dimension of the unlocking body at the unlocking surface; and
a grip accessory, comprising:
a grip accessory housing comprising a generally hollow body for supporting the manual injection device therein, the grip accessory housing comprising:
a distal portion having a distal end comprising a first opening adapted to receive the manual injection device;
a proximal portion comprising a second opening through which a needle of the manual injection device is extendable, the proximal portion comprising a skin contacting surface at a proximal end of the grip accessory housing; and
an intermediate portion extending between the proximal and distal portions, wherein the unlocking body is more flexible than the distal end of the grip accessory housing.

12. The injection device of claim 10, wherein the at least one movable latch comprises at least one deflectable latching arm moveable from a first position in which it causes the safety shield to be retained in its retracted position, and a second position, in which it no longer retains the safety shield in its retracted position; and
wherein the plunger is configured to move the at least one flexible latch arm from its first position to its second position when it is moved from its distal position to its proximal position.

13. The injection device of claim 10, wherein the unlocking body comprises an annular projection extending from the body of the plunger and spaced from the actuation surface of the plunger.

14. The injection device of claim 10, wherein the plunger comprises a distal portion and a proximal portion, wherein:
the distal portion has a first cross-sectional diameter;
the proximal portion has a second cross-sectional diameter; and
wherein the first cross-sectional diameter is greater than the second cross-sectional diameter and wherein the distal end of the distal portion comprises the actuation surface and the proximal end of the distal portion comprises the unlatching portion.

15. The injection device of claim 10, wherein the grip accessory further comprises a retractable sheath movable between an extended position in which the sheath extends over the proximal end of the needle and a retracted position, in which the needle extends from the retractable sheath.

16. The injection device of claim 15, wherein the retractable sheath is retractable to a position in which its proximal end does not extend from the plane defined by the skin contacting surface.

17. The grip accessory of claim 6, wherein the unlocking body is positionally fixed to the plunger rod such that movement of the plunger rod causes a corresponding movement of the unlocking body.

18. The injection device of claim 11, wherein the plunger comprises a plunger rod, and the unlocking body is positionally fixed to the plunger rod such that movement of the plunger rod causes a corresponding movement of the unlocking body.

19. The injection device of claim 11, wherein the unlocking body comprises an annular projection, flange, or disc extending from a body of the plunger and spaced from the actuation surface of the plunger.

\* \* \* \* \*